United States Patent
Pieper et al.

(10) Patent No.: US 10,174,060 B2
(45) Date of Patent: Jan. 8, 2019

(54) PROCESS FOR PURIFYING MONOOCTYLIN TRICHLORIDE

(71) Applicant: CHEMTURA CORPORATION, Midlebury, CT (US)

(72) Inventors: Thomas Pieper, Bergkamen (DE); Oliver Schumacher, Werne (DE); Damian Kielbus, Kamen (DE); Detlef Massing, Werne (DE)

(73) Assignee: LANXESS Organometallics GmbH, Bergkamen (DE)

( * ) Notice: Subject to any disclaimer, the term of this patent is extended or adjusted under 35 U.S.C. 154(b) by 0 days.

(21) Appl. No.: 15/538,228

(22) PCT Filed: Oct. 13, 2015

(86) PCT No.: PCT/IB2015/001866
§ 371 (c)(1),
(2) Date: Jun. 21, 2017

(87) PCT Pub. No.: WO2016/103011
PCT Pub. Date: Jun. 30, 2016

(65) Prior Publication Data
US 2017/0334935 A1  Nov. 23, 2017

(30) Foreign Application Priority Data

Dec. 23, 2014 (EP) .................................. 14200184

(51) Int. Cl.
*C07F 7/22* (2006.01)
(52) U.S. Cl.
CPC .......... *C07F 7/2296* (2013.01); *C07F 7/2208* (2013.01)

(58) Field of Classification Search
None
See application file for complete search history.

(56) References Cited

U.S. PATENT DOCUMENTS

| | | | |
|---|---|---|---|
| 3,248,411 A | 4/1966 | Neumann et al. | |
| 6,768,017 B2 | 7/2004 | Thoonen et al. | |
| 6,846,944 B2 | 1/2005 | Schumacher et al. | |
| 7,592,472 B2 | 9/2009 | Boele et al. | |

FOREIGN PATENT DOCUMENTS

| | | |
|---|---|---|
| GB | 1501673 A | 2/1978 |
| JP | S57-106685 A | 7/1982 |
| JP | S57-106686 A | 7/1982 |

OTHER PUBLICATIONS

JPS57106685 machine translation, translated in 2018.*
PCT International Search Report dated Jan. 20, 2016 from corresponding Application No. PCT/IB2015/001866.

* cited by examiner

*Primary Examiner* — Clinton A Brooks

(57) ABSTRACT

The present invention provides a process for producing monooctyltin trichloride comprising very low levels of dioctyltin and trioctyltin compounds, said process comprising the following steps: (1) Contacting an organotin chloride mixture comprising monooctyltin chloride with an aqueous phase containing halide ions, said step optionally being carried out in the presence of organic solvent; (2) separating the resulting aqueous phase which is rich in monooctyltin chloride from the organic phase containing most of the dioctyltin and trioctyltin compounds; (3) optionally purifying said aqueous phase comprising monooctyltin trichloride from undesired side products by washing said aqueous phase with an organic solvent; and (4) recovering monooctyltin trichloride from said aqueous phase comprising monooctyltin trichloride.

17 Claims, No Drawings

PROCESS FOR PURIFYING MONOOCTYLIN TRICHLORIDE

The present invention relates to an improved process for purifying monooctyltin trichloride.

For many years monoalkyltin trichlorides ($RSnCl_3$) are industrially used on a large scale, e.g. as precursors for CVD coating of glass, and as raw materials for the production of organotin catalysts and organotin PVC heat stabilizers.

Within the family of organotin compounds, methyltin, butyltin, and octyltin compounds (those with methyl, butyl, and octyl groups bound to tin) are technically particularly important.

Within those compounds, the monoalkyltin compounds ($RSnX_3$, with only one alkyl group bound to tin) have generally the lowest toxicity, and are considered non-toxic based on present standards.

In contrast thereto, diorganotin compounds ($R_2SnX_2$) and particularly triorganotin compounds ($R_3SnX$) have generally a considerably higher toxicity (both acute and long-term toxicity).

This led to restrictions with respect to the use of dialkyltin and trialkyltin compounds in several countries throughout the world.

The European Union, for example, restricted the maximum tolerated concentration of triorganotin compounds in all consumer goods to a maximum level of 0.1% (by weight) as from Jul. 1, 2010. In addition, the European Union decided to specifically restrict the maximum tolerated concentration of dibutyltin and dioctyltin compounds in some types of consumer goods to 0.1% (by weight) as from Jan. 1, 2012, and in further types of consumer goods to 0.1% (by weight) as from Jan. 1, 2015.

Thus, it is required to have access to monoalkyltin compounds comprising very low levels of undesired diorganotin and triorganotin compounds. More specifically, monooctyltin compounds comprising levels of less than 0.3% of dioctyltin dichloride and less than 0.1% trioctyltin chloride impurities are required.

DESCRIPTION OF THE PRIOR STATE OF THE ART

Various methods have been described or suggested for the industrial production of monoalkyltin trichlorides $RSnCl_3$.

A) The most common method is a multistep process comprising:
(1) A first step wherein higher alkylated tin compounds (di-, tri-, or tetraorganotin compounds, or mixtures of them) are formed by alkylation of inorganic tin compounds;
(2) subsequent steps (described e.g. in U.S. Pat. No. 3,248,411) wherein said higher alkylated alkyl tin compounds are reacted with tin tetrachloride (stannic (IV) chloride, $SnCl_4$) in order to form mixtures containing monoalkyltin trichlorides (this general procedure is sometimes called redistribution, scrambling, or comproportionation).

A fundamental drawback of this process is that it does not yield monoalkyltin trichlorides comprising low levels of diorganotin and triorganotin compounds.

The generally accepted explanation is that the redistribution of diorganotin compounds with $SnCl_4$ is kinetically hindered, and might even be completely blocked if the alkyl group bound to tin has four or more carbon atoms. When the redistribution does not start from diorganotin, but from tri- or tetraorganotin compounds, stoichiometric amounts of diorganotin compounds are formed as by-products, and remain in the product mixture. For example, in the industrially important redistribution of tetrabutyltin and $SnCl_4$ to monobutyltin trichloride, the amount of dibutyltin dichloride by-product is at least 33%.

B) U.S. Pat. No. 6,768,017 suggests adding transition metal-based catalysts in order to facilitate a kinetically hindered redistribution of diorganotin compounds with $SnCl_4$ so as to form monoalkyltin trichlorides. The only catalysts demonstrated to work according to U.S. Pat. No. 6,768,017 are compounds of precious metals (Pd or Pt). It remained, however, unproven that said catalysts could be satisfactorily recovered after reaction and be re-used. This process appears economically unattractive, because reported yields are unsatisfactory, reported selectivity is low, reported reaction times are long, and it requires expensive catalysts.

Furthermore, U.S. Pat. No. 7,592,472 suggests producing monoalkyltin trichlorides by reaction of $SnCl_2$, alkenes and HCl in the presence of transition metal-based catalysts. The only catalysts demonstrated to work are compounds of precious metals (Pd or Pt) used in a high concentration, and it remained unproven that said catalysts could be satisfactorily recovered after reaction, and re-used. This process appears economically unattractive, because reported yields are unsatisfactory, reported selectivity is low, and it requires expensive catalysts.

C) GB 1 501 673 and U.S. Pat. No. 6,846,944 teach that mixtures of monoalkyltin trichlorides and diorganotin dichloride compounds can be prepared by partial alkylation of $SnCl_4$ with aluminum alkyl donor complexes. As described in GB 1 501 673 in view of the commercial availability and low costs of the components preferred aluminum alkyl donor complexes are complexes of trialkylaluminum compounds ($AlR_3$) with ethers. Also the method described in these documents does not allow direct production of monoctyltin trichloride with the desired low levels of dioctyltin and trioctyltin compounds.

For the manufacturing of pure monobutyltin trichloride (an industrially important compound used for pyrolytic glass coating and the production of monobutyltin catalysts and stabilizers) it is state of the art to first produce by one of the afore mentioned methods A) to C) a mixture comprising monobutyltin trichloride and dibutyltin dichloride, and subsequently to separate the resulting mixture by physical means.

A preferred method of separation is a fractional distillation (this is possible, because the vapor pressure of monobutyltin trichloride is acceptably high and separation factors of dibutyltin dichloride are high). But it is also possible to selectively dissolve the monobutyltin trichloride in water and to recover it later from the aqueous solution (this is possible, because monobutyltin trichloride is miscible with water, while dibutyltin dichloride is practically insoluble in water).

Pure monooctyltin trichloride cannot easily be produced in the same way. Separation of mixtures of monooctyltin trichloride and dioctyltin dichloride by distillation is difficult, because the vapor pressure of monooctyltin trichloride is low and separation factors of dioctyltin dichloride are not favorable; and more importantly at high temperature and low pressure the thermal degradation of monooctyltin trichloride increases, negatively effecting product yields and economics. It is also not possible to selectively dissolve the monooctyltin trichloride component into water, because monooctyltin trichloride is practically insoluble in water.

Hence, it is still desirable to provide a process which allows a straightforward production of very pure monooctyltin trichloride comprising very low levels of dioctyltin and trioctyltin compounds. More specifically, levels of less than 0.3% of dioctyltin dichloride and less than 0.1% trioctyltin chloride impurities are required.

DESCRIPTION OF THE INVENTION

It has now been found that monooctyltin trichloride comprising very low levels of dioctyltin and trioctyltin compounds can be obtained from organotin chloride mixtures comprising monooctyltin trichloride, said process comprising the following steps:
(1) Contacting an organotin chloride mixture comprising monooctyltin chloride with an aqueous phase containing halide ions, said step optionally being carried out in the presence of organic solvent (in the following this step will also be referred to as "extraction" step);
(2) separating the resulting aqueous phase which is rich in monooctyltin chloride from the organic phase containing most of the dioctyltin and trioctyltin compounds (in the following this step will also be referred to as "phase separation" step);
(3) optionally purifying said aqueous phase comprising monooctyltin trichloride from undesired side products by washing said aqueous phase with an organic solvent (in the following this step will also be referred to as "scrubbing" step); and
(4) recovering monooctyltin trichloride from said aqueous phase comprising monooctyltin trichloride (in the following this step will also be referred to as "recovery" step).

Thus, the present invention provides a process for producing monooctyltin trichloride comprising very low levels of dioctyltin and trioctyltin compounds, said process comprising the following steps:
(1) Contacting an organotin chloride mixture comprising monooctyltin chloride with an aqueous phase containing halide ions, said step optionally being carried out in the presence of organic solvent (in the following this step will also be referred to as "extraction" step);
(2) separating the resulting aqueous phase which is rich in monooctyltin chloride from the organic phase containing most of the dioctyltin and trioctyltin compounds (in the following this step will also be referred to as "phase separation" step);
(3) optionally purifying said aqueous phase comprising monooctyltin trichloride from undesired side products by washing said aqueous phase with an organic solvent (in the following this step will also be referred to as "scrubbing" step); and
(4) recovering monooctyltin trichloride from said aqueous phase comprising monooctyltin trichloride (in the following this step will also be referred to as "recovery" step).

DETAILED DESCRIPTION OF THE INVENTION

Usually, monooctyltin trichloride can be produced by monoalkylation of tin tetrachloride with trioctyl aluminum in form of a donor complex with an ether or a tertiary amine. Alternatively, monooctyltin trichloride can also be produced by a redistribution reaction of tin tetrachloride with tetraoctyltin, such as by a process as described in U.S. Pat. No. 3,248,411.

Examples of suitable aluminum trioctyl aluminum compounds to be used according to the present invention are e.g., tri-n-octylaluminum, and tri-iso-octylaluminum.

Suitable donor complexes of the trioctyl aluminum compound include, for example, complexes with symmetrical or asymmetrical, saturated or unsaturated, linear or branched aliphatic, aromatic or cyclic ethers or amines. Factors for choosing the appropriate ether or amine are, e.g.: commercial availability, costs, safety properties (flammability, flash point, toxicity, tendency to form hazardous peroxides), physical properties (water solubility, freezing point, boiling point, vapor pressure), ease of separation form the products, and ease of recycling.

Examples of suitable ethers and amines are diethyl ether, di-n-butyl ether, methyl-tert.-butyl ether, tetrahydrofuran, dioxane, anisole, and triethylamine, pyridine and dimethylaniline.

Some donor complexes, for example, those with tetrahydrofuran or pyridine, alkylate $SnCl_4$ to form a mixture of products $R_nSnCl_{4-n}$, wherein n represents 1 to 4 and R represents an alkyl group as defined above, but in which the alkyl-tin trichloride is the main constituent.

Complexes of di-n-butyl ether with a trioctyl-aluminum compound have proved especially favourable. In a more preferred embodiment the $SnCl_4$ starting material is also used as an etherate complex. Complexes of $SnCl_4$ with other ethers or with amines may also be used.

The reaction usually is carried out in such a way that the tin tetrachloride is initially placed in the reaction vessel, whereupon the donor complex of the trioctyl aluminum compound is added thereto. By first providing the tin halide and subsequently adding the donor complex, one can more easily assure that the aluminum alkyl compound is not present in excess amount in the reaction medium.

Additional reactants or ingredients may also be included with the aluminum trioctyl being used in the form of a donor complex with an ether or a tertiary amine, such as a solvent or mixture of solvents. The solvent may be an inert organic solvent, such as hexane, isooctane, benzene, toluene, kerosene, cyclohexane, chlorobenzene etc. A suitable other solvent, e.g., an ether, such as tetrahydrofuran, diethylether, or dibutylether, may also be used. A catalyst may or may not be included in the reaction. In a preferred embodiment, no catalysts, such as precious metal catalysts, are included in the reaction medium.

The reaction is usually conducted at a temperature range of from 5° C. to less than 35° C., preferably at a temperature range of from 10 to 30° C., especially 20 to 25° C., more especially 22 to 25° C.

In the process for producing octyltin trichloride the tin tetrachloride starting material is transformed into the octyltin trichloride product. Any suitable type and amount of tin tetrachloride compound may be used from any suitable source. The tin tetrachloride may be used neat or pre-dissolved in a solvent, e.g., alkanes, such as hexanes, or aromatics, such as toluene.

Additional reactants or ingredients may also be included with the tin tetrachloride, such as a solvent or mixture of solvents. The solvent may be an inert organic solvent, such as hexane, isooctane, benzene, toluene, kerosene, cyclohexane, chlorobenzene etc. A suitable other solvent, e.g., an ether, such as tetrahydrofuran, diethylether, or dibutylether, may also be used, although ethers are less preferred. A catalyst may or may not be included in the reaction. In a preferred embodiment, no catalysts, such as precious metal catalysts, are included in the reaction medium.

Suitably, the trioctyl aluminum compound is mixed with the desired donor in a manner known per se in a suitable apparatus under a protective gas. The octyl-aluminum complex compound so formed is then reacted, also under a protective gas, with the tin chloride or, if desired, with a mixture of the tin chloride and donor, e.g. di-n-butyl ether, in a molar ratio such that there is no more than one octyl group for each Sn atom. As outlined above, typically the $SnCl_4$ is first placed in the apparatus and the octyl-aluminum complex compound is run in while mixing well. As this is an exothermic process cooling is necessary to maintain a low temperature as defined above during the reaction. Preferably the reaction is carried out at a temperature in the range of from 20 to 30° C., especially 20 to 25° C., more especially 22 to 25° C.

When the conversion is finished, the reaction mixture optionally after removing the solvent which may be present is subjected to the process claimed according to the present invention. In the following said process will be described in more detail:

Extraction and Phase Separation Steps:

According to the present invention the halide ions present in the aqueous phase, usually are chloride ions. Examples of suitable sources of chloride ions present in the aqueous phase are hydrochloric acid and/or soluble chloride salts of non-toxic metals, which do not interact with monooctyltin trichloride in an undesired way.

Examples of suitable chloride salts to be used include aluminum chloride and sodium chloride. An especially preferred source of chloride ions is hydrochloric acid.

Preferably, the amount of halide ions contained in the aqueous phase is such that the molar amount of halide present in the aqueous phase, is equal to or less than the molar amount of monooctyltin trichloride to be extracted, more preferably the amount of halide ions is in a range of from 100 to 300%, even more preferably 200 to 270% of the molar amount of monooctyltin trichloride to be extracted.

Without limiting the scope of invention, it is assumed that the monooctyltin trichloride extracted into the aqueous phase may exist in the form of hydrated octyltin tetrachloro complexes $[C_8H_{17}SnCl_4]^-$ and/or octyltin pentachloro complexes $[C_8H_{17}SnCl_5]^{2-}$.

The halide ions are typically dissolved in demineralized water so as to form the aqueous phase containing halide ions.

Usually, the organotin chloride mixture is contacted with the aqueous phase containing halide ions at a temperature of from 0° C. to 100° C., more preferably at a temperature of from 20° C. to 50° C., most preferably at a temperature of from 40 to 50° C.

As an organic solvent which optionally may also be present in said extraction step, organic solvents which are immiscible with water, could be used. Non-limiting examples of such organic solvents are aromatic, aliphatic and cyclo-aliphatic hydrocarbons, ethers and ketones, preferably, ethers or aliphatic and cyclo-aliphatic hydrocarbons with 5-9 carbon atoms, and mixtures of these, more preferably di-n-butyl ether, hexane, heptane, and octane, even more preferably hexane, heptane, and octane. One typical example of such an organic solvent is "Exxsol 100-120".

If the organotin chloride mixture is contacted with the aqueous phase containing halide ions, as a dispersion or solution in an organic solvent, the organotin chloride mixture is present in the organic solvent in a concentration of 10 to 90% by weight, preferably 20 to 60% by weight, based on the amount of organic solvent used.

It is noteworthy that although di-n-butyl ether has little solubility in water, aqueous phases containing halide ions, are capable of dissolving some amounts of di-n-butyl ether.

Typically, the step of contacting an organotin chloride mixture comprising monooctyltin chloride with an aqueous phase containing halide ions according to the present invention is effected by adding an aqueous phase containing halide ions to the organotin chloride mixture and mixing said organotin chloride mixture with said aqueous phase containing halide ions for 1 to 60 minutes, preferably, for 5 to 30 minutes, more preferably for 5 to 15 minutes. Said mixing step can be effected in any way known to a person skilled in the art, and typically comprises using mechanical stirrers, static mixers, jets or other shaking measures.

After having contacted an organotin chloride mixture comprising monooctyltin chloride with an aqueous phase containing halide ions according to the present invention as described above, typically the mixing is stopped whereby two phases (an organic phase and an aqueous phase) are formed. Thereafter, the aqueous phase can be separated. Such a separation can be effected in any way known to a person skilled in the art such as decanting or separation by using a separating funnel.

Scrubbing Step:

After having separated the aqueous phase, an optional purification of said monooctyltin trichloride containing aqueous phase can be effected, for example, in order to remove by-products from the aqueous phase.

The most important by-product to be removed from the aqueous phase, is dioctyltin dichloride and/or trioctyltin chloride. It is noteworthy that although dioctyltin dichloride and trioctyltin chloride are practically insoluble in water, aqueous phases comprising halide ions, are capable of extracting some dioctyltin dichloride and/or trioctyltin chloride.

Suitable organic solvents to be used according to the present invention for purifying the aqueous phase are organic solvents immiscible with water, but capable of dissolving undesired by-products, such as dioctyltin dichloride. Non-limiting examples of suitable organic solvents to be used in said scrubbing step are aromatic, aliphatic and cyclo-aliphatic hydrocarbons, ethers and ketones, preferably ethers or aliphatic and cyclo-aliphatic hydrocarbons having 5 to 9 carbon atoms, and mixtures of these, more preferably hexane, heptane, and/or octane. One practical example of a suitable extracting solvent is "Exxsol 100-120" sold by Exxon.

If the organic solvent to be used for said purification is also capable of dissolving monooctyltin chloride (such as for example di-n-butyl ether), the organic solvent should be used in a way that undesired re-extraction of monooctyltin trichloride from the aqueous phase is avoided or at least limited. Suitable ways to limit or even to avoid extraction of monooctyltin trichloride from the aqueous phase are for example to use only small amounts of solvent, i.e., to use a low weight ratio of organic solvent to aqueous phase, and/or to carry out said purification step at low temperatures of from 20 to 50° C.

In a preferred embodiment the purification step according to the present invention is carried out at a temperature of from 20 to 50° C. in such a way that the weight ratio of organic solvent/aqueous phase 10 to 20/100 based on the weight of both phases.

In a preferred embodiment said purification step is repeated one or more times, more preferably two to three times.

Recovery:

After the aqueous phase was optionally subjected to a purification step as described above, monooctyltin trichloride is recovered from the aqueous phase comprising monooctyltin trichloride. Such a recovery can be done in any way known to a person skilled in the art.

If for example the source of halide ions in step (1) outlined above is hydrochloric acid, water and hydrochloric acid can be simply distilled off, in order to obtain monooctyltin trichloride.

It is also possible to recover monooctyltin trichloride from the aqueous phase with a suitable amount of organic solvent, and subsequently to distill off the organic solvent in order to obtain the pure monooctyltin trichloride product.

Non-limiting examples of suitable solvents to be used for the recovery according to the present invention are aromatic, aliphatic and cyclo-aliphatic hydrocarbons, ethers and ketones.

Preferred solvents according to the present invention are ethers, more preferably di-n-butyl ether.

According to the present invention recovery of the monooctyltin trichloride product can be done at a temperature in a range of from 0 to 100° C., preferably at a temperature in a range of from 40 to 70° C.

Alternatively, monooctyltin trichloride dissolved in the aqueous phase can be recovered by chemically converting monooctyltin trichloride into another stable monooctyltin compound.

For example, the aqueous phase can be neutralized with a suitable base, such as sodium hydroxide, ammonium hydroxide, or ammonia, so that monooctyltin oxide and/or hydroxyoctyloxostannane will be formed. As monooctyltin oxide and/or hydroxyoctyloxostannane is a solid material, it can be easily separated from the aqueous phase by filtration. Monooctyltin oxide and hydroxyoctyloxostannane are well known esterification catalysts, and raw materials for producing PVC heat stabilizers.

As a further example, the aqueous phase can be neutralized with a suitable base in the presence of stoichiometric amounts of mercaptides, such as isooctyl mercaptoacetate, 2-ethylhexyl mercaptoacetate, or dodecylmercaptane, so that a monooctyltin mercaptide will be formed, which can be easily separated from the aqueous phase because it has a low solubility in the aqueous phase. Certain monooctyltin mercaptides are well known and commercially important PVC heat stabilizers.

The following Examples illustrate the invention:

EXAMPLES

General Instructions:

If not mentioned to the contrary, in all the examples described the extraction, scrubbing, and re-extraction steps were performed in laboratory glass double wall vessels having an operable volume of 0.25 to 1 liter, equipped with a mechanical stirrer, dropping funnel, thermostat, optional inlet for inert gas ($N_2$), and gas outlet for pressure equilibration; all phase separations were performed in laboratory glass separation funnels having volumes of 0.1 to 1 liter. Typical stirring speeds used in the following Examples were in a range of from 100 rpm to 500 rpm.

The term "other tin compounds" used thereafter refers to organotin compounds containing alkyl groups other than n-octyl, which are common by-products in technical octyltin mixtures, as well as inorganic tin tetrachloride. All tin species composition analytics were performed by GC (gas chromatography).

Example 1

This Example demonstrates the extraction of mono-n-octyltin trichloride from a mixture of organotin chlorides into an aqueous phase comprising hydrochloric acid, the fact that some di-n-butyl ether is soluble in an aqueous phase comprising mono-n-octyltin trichloride, the scrubbing of the aqueous phase with small amounts of di-n-butyl ether, and the re-extraction of mono-n-octyltin trichloride from aqueous phase by larger amounts of di-n-butyl ether.

A technical raw organotin chloride mixture had a tin species composition of 64.2% mono-n-octyltin trichloride, 33.8% di-n-octyltin dichloride, 0.2% tri-n-octyltin chloride, and 1.8% other tin compounds.

Step 1: Aqueous Extraction:

To 97.5 g of this raw organotin chloride mixture 58.0 g of 16% aqueous HCl solution were added. The mixture was heated to 50° C. and stirred for ca. 10 minutes. After the stirring stopped, 2 phases appeared; they were allowed to settle, and subsequently separated. The upper (organic) phase had a weight of 33.3 g; it had a tin species composition of 25.6% mono-n-octyltin trichloride, 71.7%, di-n-octyltin dichloride, 0.5% tri-n-octyltin chloride, and 2.2% other tin compounds. The lower (aqueous) phase was further treated as described below.

Step 2: Scrubbing of the Aqueous Phase to Remove Dioctyl and Trioctyltin Chlorides:

First scrubbing: To 105 g of the aqueous phase resulting from step 1, 15 g of di-n-butyl ether were added, whereupon the mixture was stirred at room temperature. After the stirring was terminated, 2 phases appeared; they were allowed to settle, and subsequently separated. The upper (organic) phase had a weight of 10.5 g; it comprised a tin species composition of 75.6% mono-n-octyltin trichloride, 22.7% di-n-octyltin dichloride, 0.1% tri-n-octyltin chloride, and 1.6% other tin compounds.

Second scrubbing: To the resulting aqueous phase obtained from the first scrubbing, another 5 g of di-n-butyl ether were added, and the mixture was stirred at room temperature. After the stirring was terminated, 2 phases appeared; they were allowed to settle, and subsequently separated. The upper (organic) phase had a weight of 7.7 g; it comprised a tin species composition of 84.7% mono-n-octyltin trichloride, 13.6% di-n-octyltin dichloride, 0.0% tri-n-octyltin chloride, and 1.7% other tin compounds. The lower (aqueous) phase was further treated as described below.

Step 3: Recovery of Monooctyltin Trichloride from the Aqueous Phase:

First re-extraction: To 103.9 g of the aqueous phase resulting from step 2, 35 g of di-n-butyl ether were added, and the mixture was stirred at room temperature. After the stirring was terminated, 2 phases appeared; they were allowed to settle, and subsequently separated. The upper (organic) phase had a weight of 80.4 g; it had a tin species composition of 96.4% mono-n-octyltin trichloride, 2.1% di-n-octyltin dichloride, 0.0% tri-n-octyltin chloride, and 1.5% other tin compounds.

Second re-extraction: To 57.6 g of the aqueous phase resulting from the first re-extraction, 19.0 g of di-n-butyl ether were added, and the mixture was stirred at room temperature. After the stirring was terminated, 2 phases appeared; they were allowed to settle, and subsequently separated. The upper (organic) phase had a weight of 29.9 g; it had a tin species composition of 98.2% mono-n-octyltin trichloride, 0.2% di-n-octyltin dichloride, 0.0% tri-n-octyltin chloride, and 1.6% other tin compounds.

Third re-extraction: To 46.4 g of the aqueous phase resulting from the second re-extraction, 15.0 g of di-n-butyl ether were added, and the mixture was stirred at room temperature. After the stirring was terminated, 2 phases appeared; they were allowed to settle, and subsequently separated. The upper (organic) phase had a weight of 15.9 g; it had a tin species composition of 90.6% mono-n-octyltin trichloride, 0.8% di-n-octyltin dichloride, 0.0% tri-n-octyltin chloride, and 8.4% other tin compounds.

Example 2

This Example demonstrates the extraction of mono-n-octyltin trichloride from a mixture of organotin chlorides and n-heptane as organic solvent added to an aqueous phase comprising hydrochloric acid, the scrubbing of the aqueous phase with small amounts of n-heptane, and the recovery of mono-n-octyltin trichloride from aqueous phase by di-n-butyl ether.

A technical raw organotin chlorides mixture had a tin species composition of 61.8% mono-n-octyltin trichloride, 32.9% di-n-octyltin dichloride, 0.2% tri-n-octyltin chloride, and 3.5% other tin compounds.

100.0 of this mixture were diluted with 50.0 g n-heptane.

Step 1: Aqueous Extraction:

To 150.0 g of this diluted raw organotin chlorides mixture 87.0 g of 16% aqueous HCl solution were added. The mixture was heated to 50° C. and stirred for ca. 10 minutes. After the stirring was terminated, 2 phases appeared; they were allowed to settle, and subsequently separated. The upper (organic) phase had a weight of 92.0 g; it had a tin species composition of 22.4% mono-n-octyltin trichloride, 69.9% di-n-octyltin dichloride, 0.5% tri-n-octyltin chloride, and 7.2% other tin compounds. The lower (aqueous) phase was treated further as described below.

Step 2: Scrubbing of the Aqueous Phase to Remove Dioctyl and Trioctyltin Chlorides:

First scrubbing: To 145 g of the aqueous phase resulting from step 1, 14.5 g of n-heptane were added, and the mixture was stirred at room temperature. After the stirring was terminated, 2 phases appeared; they were allowed to settle, and subsequently separated. The upper (organic) phase had a weight of 13.3 g; it had a tin species composition of 61.8% mono-n-octyltin trichloride, 31.6% di-n-octyltin dichloride, 0.0% tri-n-octyltin chloride, and 6.6% other tin compounds.

Second scrubbing: To the resulting aqueous phase from the first scrubbing, another 14 g of n-heptane were added, and the mixture was stirred at room temperature.

After the stirring was terminated, 2 phases appeared; they were allowed to settle, and subsequently separated. The upper (organic) phase had a weight of 13.311 g; it had a tin species composition of 86.2% mono-n-octyltin trichloride, 10.8% di-n-octyltin dichloride, 0.0% tri-n-octyltin chloride, and 3.0% other tin compounds. The lower (aqueous) phase was treated further as described below.

Step 3: Recovery of Monooctyltin Trichloride from the Aqueous Phase:

First re-extraction: To 140.0 g of the aqueous phase resulting from step 2, 28.5 g of di-n-butyl ether were added, and the mixture was stirred at room temperature. After the stirring was terminated, 2 phases appeared; they were allowed to settle, and subsequently separated. The upper (organic) phase had a weight of 51.8 g; it had a tin species composition of 98.7% mono-n-octyltin trichloride, 0.17% di-n-octyltin dichloride, 0.0% tri-n-octyltin chloride, and 2.0% other tin compounds.

Second re-extraction: To 117.8 g of the aqueous phase resulting from the first re-extraction, 23.6 g of di-n-butyl ether were added, and the mixture was stirred at room temperature. After the stirring was terminated, 2 phases appeared; they were allowed to settle, and subsequently separated. The upper (organic) phase had a weight of 58.4 g; it had a tin species composition of 99.0% mono-n-octyltin trichloride, 0.07% di-n-octyltin dichloride, 0.0% tri-n-octyltin chloride, and 1.9% other tin compounds.

Third re-extraction: To 82.5 g of the aqueous phase resulting from the second re-extraction, 16.5 g of di-n-butyl ether were added, and the mixture was stirred at room temperature. After the stirring was terminated, 2 phases appeared; they were allowed to settle, and subsequently separated. The upper (organic) phase had a weight of 17.2 g; it had a tin species composition of 94.1% mono-n-octyltin trichloride, 0.3% di-n-octyltin dichloride, 0.0% tri-n-octyltin chloride, and 5.6% other tin compounds. The lower (aqueous) phase was analyzed by ICP for residual metal; it had a content of 0.7% tin.

Example 3

This Example demonstrates the extraction of mono-n-octyltin trichloride from a mixture of organotin chlorides into an aqueous phase comprising hydrochloric acid, the scrubbing of the aqueous phase with small amounts of n-heptane, and the recovery of monooctyltin trichloride from the aqueous phase by distillation of the aqueous HCl.

A technical raw organotin chlorides mixture had a tin species composition of 60.7% mono-n-octyltin trichloride, 36.9% di-n-octyltin dichloride, 0.3% tri-n-octyltin chloride, and 2.1% other tin compounds; by elementary analysis it contained 36.9% tin.

Step 1: Aqueous Extraction.

201 g of this raw organotin chlorides mixture were extracted with 161 g of 16% aqueous HCl solution at 50° C., as described in example 1. The resulting upper (organic) phase had a weight of 78.3 g; it had a tin species composition of 18.0% mono-n-octyltin trichloride, 79.1% di-n-octyltin dichloride, 0.7% tri-n-octyltin chloride, and 2.2% other tin compounds; by elementary analysis it contained 36.9% tin. The Lower (aqueous) phase was treated further as described below.

Step 2: Scrubbing of the Aqueous Phase to Remove Dioctyl and Trioctyltin Chlorides.

First scrubbing: To 137 g of the aqueous phase resulting from step 1, 27.5 g of n-heptane were added, and the mixture was stirred at 50° C. After the stirring was terminated, 2 phases appeared; they were allowed to settle, and subsequently separated. The upper (organic) phase had a weight of 32.6 g; it had a tin species composition of 25.3% mono-n-octyltin trichloride, 71.6% di-n-octyltin dichloride, 0.6% tri-n-octyltin chloride, and 2.5% other tin compounds; by elementary analysis it contained 7.1% tin.

Second scrubbing: To the resulting aqueous phase from the first scrubbing, another 12.5 g of n-heptane were added, and the mixture was stirred at 50° C. After the stirring was terminated, 2 phases appeared; they were allowed to settle, and subsequently separated. The upper (organic) phase had a weight of 14.5 g; it had a tin species composition of 51.8% mono-n-octyltin trichloride, 46.1% di-n-octyltin dichloride, 0.3% tri-n-octyltin chloride, and 1.9% other tin compounds;

by elementary analysis it contained 2.6% tin. The lower (aqueous) phase was treated further as described below.

Third scrubbing: To the resulting aqueous phase from the second scrubbing, another 12.5 g of n-heptane were added, and the mixture was stirred at 50° C. After the stirring was terminated, 2 phases appeared; they were allowed to settle, and subsequently separated. The upper (organic) phase had a weight of 13.0 g; it had a tin species composition of 85.7% mono-n-octyltin trichloride, 12.6% di-n-octyltin dichloride, 0.0% tri-n-octyltin chloride, and 1.7% other tin compounds; by elementary analysis it contained 1.7% tin.

The resulting lower (aqueous) phase had a weight of 123:5 g; it had a tin species composition of 98.5% mono-n-octyltin trichloride, 0.06% di-n-octyltin dichloride, 0.0% tri-n-octyltin chloride, and 1.4% other tin compounds; by elementary analysis it contained 14.1% tin. It was treated further as described below.

Step 3: Recovery of Monooctyltin Trichloride by Distillation of the Aqueous HCl:

110 g of the aqueous phase from step 3 were placed into a laboratory glass distillation apparatus. Hydrochloric acid and water were distilled off under mild conditions, the maximum temperature being 50° C. at 30 mbar (30 hPa).

The resulting product had a weight of 35.5 g; it had a tin species composition of 98.6% mono-n-octyltin trichloride, 0.04% di-n-octyltin dichloride, 0.0% tri-n-octyltin chloride, and 1.4% other tin compounds; by elementary analysis it contained 35.1% tin, and 31.3% Cl.

Example 4

This Example demonstrates how the solubility of mono-n-octyltin trichloride in aqueous aluminum chloride phase and its extraction from organic phase depends on the chloride concentration.

A mixture was prepared, consisting by weight of 55.7% mono-n-octyltin trichloride, 10.7% di-n-butyl ether, 26.2% n-heptane, 7.3% $AlCl_3$. 10 g of this mixture were transferred into a graduated glass cylinder.

Portions of deionized water were added stepwise to the system, and the volume changes of organic and aqueous phase were noted. Volume decrease of the organic phase indicates extraction of monooctyltin into the aqueous phase. Results reported in the table below demonstrate that extraction is poor with concentrated aqueous aluminum chloride solution, improves upon dilution and becomes particularly efficient, when the aqueous aluminum chloride solution is only approx. 17% or less concentrated.

| Added water Volume (mL) | aqueous $AlCl_3$ concentration (%) | Organic phase Volume (mL) |
| --- | --- | --- |
| 0 | | 9 |
| 1.5 | 33 | 6.7 |
| 1.8 | 29 | 6.3 |
| 2.1 | 26 | 6.5 |
| 2.4 | 23 | 6.3 |
| 2.7 | 21 | 6.1 |
| 3.0 | 20 | 5.5 |
| 3.3 | 18 | 4.7 |
| 3.6 | 17 | 1.9 |
| 3.9 | 16 | 1.8 |
| 4.2 | 15 | 1.8 |
| 4.5 | 14 | 1.9 |
| 4.8 | 13 | 1.8 |
| 5.1 | 13 | 1.9 |
| 5.4 | 12 | 1.9 |

Example 5

This Example demonstrates how the solubility of mono-n-octyltin trichloride in aqueous hydrochloric acid phase and its extraction from organic phase depends on the chloride concentration.

20.3 g of mono-n-octyltin trichloride, 3.9 g of di-n-butyl ether and 9.5 g of n-heptane were mixed to give of clear and homogeneous solution. 8.6 g (7.4 mL) of a 32% aqueous HCl solution were added. The mixture was stirred for ca. 10 minutes, and then transferred into a graduated glass cylinder. 2 phases appeared; they were allowed to settle.

Portions of deionized water were added stepwise to the system, and the volume changes of organic and aqueous phases were noted. Volume decrease of the organic phase indicates extraction of monooctyltin into the aqueous phase. Results reported in the table below demonstrate that extraction is poor with concentrated hydrochloric acid, improves upon dilution and becomes particularly efficient when the HCl concentration is approx. 16%.

| Added water Volume (mL) | aqueous HCl concentration (%) | Organic phase Volume (mL) | Aqueous phase Volume (mL) |
| --- | --- | --- | --- |
| 0 | 32.0 | 32 | 8 |
| 1 | 28.7 | 22 | 20 |
| 2 | 26.0 | 21 | 21 |
| 3 | 23.7 | 18 | 25 |
| 4 | 21.8 | 15 | 28 |
| 5 | 20.2 | 15 | 29 |
| 6 | 18.8 | 13.5 | 31 |
| 7 | 17.6 | 12 | 33 |
| 8 | 16.6 | 11 | 35 |
| 9 | 15.6 | 10 | 37 |
| 11 | 14.0 | 11 | 38 |
| 16 | 11.2 | 12 | 40 |

Example 6

This Example demonstrates how the solubility of mono-n-octyltin trichloride in aqueous aluminum chloride phase and its extraction from organic phase depends on the temperature.

A mixture was prepared, consisting by weight of 55.7% mono-n-octyltin trichloride, 10.7% di-n-butyl ether, 26.2% n-heptane, 7.3% $AlCl_3$. To 20 g of this mixture (having a volume of 18.5 mL), 8.4 g of deionized water were added under stirring, and the resulting mixture was placed into a graduated glass cylinder.

The temperature in the glass cylinder was adjusted to 20° C., and the phases were allowed to settle and separate for 30 minutes. The resulting volume of the organic phase was 8 mL.

Subsequently, the temperature in the glass cylinder was adjusted to 40° C., and the phases were allowed to settle and separate for 30 minutes. The resulting volume of the organic phase was 10 mL.

Subsequently, the temperature in the glass cylinder was adjusted to 60° C., and the phases were allowed to settle and separate for 30 minutes. The resulting volume of the organic phase was 14 mL.

Example 7

This Example demonstrates that mono-n-octyltin trichloride can be extracted with aqueous sodium chloride phase.

10.15 g of mono-n-octyltin trichloride, 1.95 g of di-n-butyl ether and 4.75 g of n-heptane were mixed to give of clear and homogeneous solution. The organic mixture had a volume of 16 mL. 2.5 g of a saturated NaCl solution was added. The mixture was stirred for ca. 10 minutes, and then transferred into a graduated glass cylinder. Phase separation could not be observed, because a suspension had formed. When further 5 g of deionized water were added and the mixture was heated to 45° C., 2 phases appeared. When they had settled, it became visible, that the volume of the organic phase was reduced from 16 mL to ca. 8 mL, indicating extraction of monooctyltin trichloride into the aqueous phase. Upon cooling to room temperature, the lower aqueous phase solidified.

The invention claimed is:

1. A process for producing monooctyltin trichloride comprising very low levels of dioctyltin and trioctyltin compounds, the process comprising:
   i) contacting an organotin chloride mixture comprising monooctyltin chloride, which organotin chloride mixture also comprises dioctyltin compounds and/or trioctyltin compounds, with an aqueous phase containing halide salts, optionally in the presence of organic solvent, resulting in an aqueous phase comprising monooctyltin chloride, and an organic phase containing most of the dioctyltin trioctyltin and/or trioctyltin compounds;
   ii) separating the aqueous phase from the organic phase;
   iii) purifying the aqueous phase from undesired side products by washing the aqueous phase with an organic solvent; and
   iv) recovering monooctyltin trichloride from the aqueous phase.

2. The process according to claim 1, wherein i), contacting the organotin chloride mixture with the aqueous phase containing halide salts, is carried out in the presence of an organic solvent.

3. The process according to claim 2, wherein the organic solvent present during i), contacting the organotin chloride mixture with the aqueous phase containing halide salts, is selected from the group consisting of n-hexane, n-heptane and di-n-butyl ether.

4. The process according to claim 3, wherein the organic solvent used in iii) to wash the aqueous phase is selected from the group consisting of n-hexane and n-heptane.

5. The process according to claim 4, wherein i), contacting the organotin chloride mixture with the aqueous phase containing halide salts in the presence of an organic solvent selected from the group consisting of n-hexane, n-heptane and di-n-butyl ether, is carried out at a temperature of 20 to 50° C.

6. The process according to claim 5, wherein iii), washing the aqueous phase with an organic solvent, is carried out at a temperature of 20 to 50° C.

7. The process according to claim 3, wherein i), contacting the organotin chloride mixture with the aqueous phase containing halide salts in the presence of an organic solvent selected from the group consisting of n-hexane, n-heptane and di-n-butyl ether, is carried out at a temperature of 20 to 50° C.

8. The process according to claim 2, wherein the organic solvent used in iii) to wash the aqueous phase is selected from the group consisting of n-hexane and n-heptane.

9. The process according to claim 2, wherein i), contacting the organotin chloride mixture with the aqueous phase containing halide salts in the presence of an organic solvent, is carried out at a temperature of 20 to 50° C.

10. The process according to claim 2, wherein iii), washing the aqueous phase with an organic solvent, is carried out at a temperature of 20 to 50° C.

11. The process according to claim 1, wherein the organic solvent used in iii) to wash the aqueous phase is selected from the group consisting of n-hexane and n-heptane.

12. The process according to claim 11, wherein i), contacting the organotin chloride mixture with the aqueous phase containing halide salts, is carried out at a temperature of 20 to 50° C.

13. The process according to claim 12, wherein iii), washing the aqueous phase with an organic solvent, is carried out at a temperature of 20 to 50° C.

14. The process according to claim 11, wherein i), contacting the organotin chloride mixture with the aqueous phase containing halide salts, is carried out at a temperature of 20 to 50° C.

15. The process according to claim 1, wherein i), contacting the organotin chloride mixture with the aqueous phase containing halide salts, is carried out at a temperature of 20 to 50° C.

16. The process according to claim 1, wherein iii), washing the aqueous phase with an organic solvent, is carried out at a temperature of 20 to 50° C.

17. The process according to claim 1, wherein the monooctyltin trichloride produced by the process comprises less than 0.3% of dioctyltin dichloride and less than 0.1% trioctyltin chloride.

* * * * *